(12) United States Patent
Rahimsobhani (10) Patent No.: US 7,942,848 B2
(45) Date of Patent: May 17, 2011

(54) MEDICAL APPARATUS FOR DISTRIBUTING A PREDETERMINED AMOUNT OF FOREIGN SUBSTANCE TO A PREDETERMINED AREA IN LIVING BODY

(76) Inventor: Nader Rahimsobhani, Tehran (IR)

( * ) Notice: Subject to any disclaimer, the term of this patent is extended or adjusted under 35 U.S.C. 154(b) by 32 days.

(21) Appl. No.: 12/473,283

(22) Filed: May 28, 2009

(65) Prior Publication Data

US 2009/0240199 A1 Sep. 24, 2009

(51) Int. Cl.
*A61M 29/00* (2006.01)
*A61M 16/00* (2006.01)
(52) U.S. Cl. .............. 604/101.02; 128/207.15
(58) Field of Classification Search .............. 604/101.02
See application file for complete search history.

(56) References Cited

U.S. PATENT DOCUMENTS

5,791,341 A * 8/1998 Bullard .................... 128/207.15
* cited by examiner

*Primary Examiner* — Nicholas D Lucchesi
*Assistant Examiner* — Jason Flick
(74) *Attorney, Agent, or Firm* — Barry Choobin; Choobin & Choobin Consultancy L.L.C (57) ABSTRACT

A multiple cuff system is disclosed which has more than one cuff some of which may be perforated or permeable in any degree or made of porous materials to let in situ delivery of different drugs, and especially local anesthetics to the target tissues that are the tissues in touch or within the vicinity of the inflated cuff. The local anesthetics suitable to be delivered via the cuff are also introduced. The preferred method for application of the multiple cuffed ETT during surgical operations, can overcome the emergence reactions commonly encountered during lighter levels of anesthesia.

10 Claims, 5 Drawing Sheets

MEDICAL APPARATUS FOR DISTRIBUTING A PREDETERMINED AMOUNT OF FOREIGN SUBSTANCE TO A PREDETERMINED AREA IN LIVING BODY

FIELD OF THE INVENTION

The present invention relates to methods of treatment of the living body and apparatus used in the inspection and treatment of diseases, wounds, and other abnormal conditions of the bodies of humans and lower animals.

BACKGROUND OF THE INVENTION

The technique entitled, "Intubation", which includes inserting a cuffed or cuff less Endo Ttracheal Tube (ETT) into the respiratory channel (i.e., the trachea) of the patient, is used to promote mechanical ventilation in surgical or intensive care settings. It is needless to mention that the cuffles tubes mentioned above are used in the case of little children.

This method is also used as a means in keeping the respiratory channels open, which is of vital importance during surgeries. During the intubation, the ETT and the cuff(s) act as foreign objects in the respiratory passages, leading to the intolerance of the patients and consequently to reactions in the air passages.

Extubation, or in other terms removal of the ETT(s) at the end of the anesthesia of the patient, also leads to reactions that are technically called "Emergence reactions" including hypertension, tachycardia, dysrythmia, increases in IOP (Intra Ocular Pressure), ICP (Intra Cranial Pressure), bucking or straining, bronchospasm, laryngospasm, glottic spasm and so on that can lead to myocardial ischemia, defective arterial oxygenation, and vomiting, which may in turn lead to serious repercussions endangering the life of the patient. Other disadvantages resulting from the application of the presently available ETTs include tearing of stitches and bleeding as a result of bucking or straining by the patient. The intolerance of the ETTs can also lead to self-extubation of these devices by the patients that may lead to a critical situation, which if not attended promptly and urgently, can lead to the catastrophic outcomes. The main reason behind such emergence reactions is the intolerance of the ETT owing to lighter planes of anesthesia towards the end of surgery and prior to extubation. The increase in blood pressure, pulse rate, IOP, and/or ICP of the patients, suffering from underlying coronary artery disease or who have undergone eye or intracranial surgeries and pregnancy induced hypertension (PIH) may lead to disastrous outcomes.

Inadvertent or unanticipated extubation may lead to laryngospasm, bronchospasm, hypoxia and/or pulmonary edema commonly encountered in all patients especially those with hyper reactive airway diseases or bronchial asthma. Also post surgical stridor, sore throat and irritable cough may also be caused due to the application of the cuffed ETTs. Many methods have been used to overcome or at least lessen these reactions in patients, which include systemic administration of opioids, sedatives, hypnotics, β blockers, Na nitroprussid local anesthetics, topically applied local anesthetics, intra-cuff administration of lidocaine, intra-cuff administration of warmed and alkalinized lidocaine, and new designs of ETT(s) such as Mallinckrodt ET, for applying local anesthetics to tracheal mucosa, using 10% lidocaine and etidocaine sprays through some channels on the ETT and the LITA ETT.

None of these methods have however been definitely and completely successful and safe in overcoming the problems mentioned above.

Tolerance of the ETTs in conscious patients with intact airway reflexes of the entire respiratory system (e.g. in the intensive care units), is almost impossible. Thus opioids and other anesthetic drugs are administered so as to increase the threshold of tolerance of the tubes by the patients and prevent self extubation and/or other possible reflexes. This however leads to a prolonged stay in the ICU and thus results in an increased risk of complications such as infections, pressure sores and narrowing of the wind pipe—the trachea.

SUMMARY OF THE INVENTION

Accordingly, it is a primary object of the present invention to provide a medical apparatus for distributing a predetermined amount of foreign substance to a predetermined area in living body consisting of: a main tube; a first cuff wherein said first cuff comprises of a predetermined size, a predetermined shape and a material wherein said material is intact or impermeable; a second cuff wherein said second cuff comprises of a predetermined size, a predetermined shape, porous material and/or permeable material or combination thereof, wherein said first cuff is embedded in said second cuff; a third cuff wherein said third cuff comprises of a predetermined size, a predetermined shape and made of material wherein said material consists of porous materials, and wherein said first cuff and said second cuff are entirely embedded in said third cuff; a first tube comprising a pilot balloon wherein said first tube is implanted to said main tube for allowing delivery of a predetermined amount of air into said first cuff; a second tube comprising a pilot balloon wherein said second tube is implanted to said main tube for allowing delivery of said predetermined amount of foreign substance to said second cuff; a third tube comprising a pilot balloon wherein said third tube is implanted to said main tube for allowing delivery of said predetermined amount of foreign substance to said third cuff.

Yet another object of the present inventions to provide a medical apparatus for distributing a predetermined amount of foreign substance to a predetermined area in living body, wherein said second cuff allows equally distributing said predetermined amount of foreign substance to said predetermined area in living body.

Yet another object of the present inventions to provide a medical apparatus for distributing a predetermined amount of foreign substance to a predetermined area in living body, wherein said second cuff is in proximal position with respect to said first cuff.

Yet another object of the present inventions to provide a medical apparatus for distributing a predetermined amount of foreign substance to a predetermined area in living body, wherein said second cuff is in distal position with respect to said first cuff.

Yet another object of the present inventions to provide a medical apparatus for distributing a predetermined amount of foreign substance to a predetermined area in living body, wherein said third cuff allows equally distributing said predetermined amount of foreign substance to said predetermined area in living body.

Yet another object of the present inventions to provides a medical apparatus for distributing a predetermined amount of foreign substance to a predetermined area in living body, wherein said pilot balloon of said second and said third tube distributes said predetermined amount of foreign substance to said predetermined area in living body in a unidirectional manner.

BRIEF DESCRIPTION OF THE DRAWINGS

a—Multiple cuffs according to the embodiments of the present invention where, the different cuffs (C1-Cn) attach the devise exactly on the same point (x and y).

b—Multiple cuff according to the embodiments of the present invention where, the different cuffs (C1-Cn) attach the devise exactly on the different points (x1 and y1) for C1 and ($x_n$ and $y_n$) for Cn.

c—Multiple cuffs according to the embodiments of the present invention showing a cuff installed at one end of a tube.

d—Multiple cuffs according to the embodiments of the present invention showing a cuff installed on a bent tube (the angle may vary).

e—Two multiple cuffs according to the embodiments of the present invention installed on a linear tube (The two cuffs may be chosen to be structurally the same or different).

P1-Pn: the pilot balloons of each cuff (The figure only depicts the m for one of the cuffs), used for injecting the drugs, or blowing of the air or other gases. The number of the pilot balloons may vary depending on the purposes.

P'1-P'n: the pilot balloons of each cuff (the figure only depicts the m for one of the cuffs), used for emptying the drugs, or sucking of the air or other gases. The number of the pilot balloons may vary depending on the purposes.

PC1-PCn: Pressure controlling valve attached to each pilot balloon P1-Pn.

PC'1-PC'n: Pressure controlling valve attached to each pilot balloon P'1-P'n.

DETAILED DESCRIPTION OF THE INVENTION

The main objective of the present invention is to design a multiple cuff built or installable on ETTs or any other cuffed devices, and the application thereof to overcome the overall problems of the traditional cuffed ETTs mentioned above.

This object is achieved by a cuff system with a plurality of different cuffs, each of which being impermeable, permeable in any degree (highly, semi, . . . ), or porous and/or mechanically and/or electrically and/or optically perforated.

According to an embodiment of the present invention, the cuff of the present invention, may also be built or installed in any numbers and/or positions on other cuffed oral or nasal ETTs and or devices like RAE Tubes, bronchial blockers, double lumen tubes, laser SLTs (Single Lumen Tube), supra glottic instruments (specially during extubation), tracheostomy tubes or in order to perform irrigation such as Broncho Alveolar Lavage (BAL), etc and so may be built or installed in instruments that may be designed in the future.

The cuff system of the present invention can have different number of cuffs (FIGS. 1 a-e) with different physical and/or chemical properties, different shapes and or different installation or fixation properties, and different number of inlets and outlets based on the goal of its application.

In case of the application of the cuff system of the present invention on ETT(s) (FIGS. 2-6), the ETT will preferably be composed of three cuffs ($C_1$, $C_2$, and $C_3$ FIG. 3) or three embedded single cuff with three proximal pilot balloons (A, $D_1$ and $D_2$, FIG. 3), each of which can serve different goals, but some of the major purposes of which may be as follows:

1—The innermost cuff or internal cuff ($C_1$, FIG. 3) is preferred to have an intact impermeable membrane and serves to fix the tube in position of desire.

2—The middle cuff ($C_2$, FIG. 3) is preferred to be permeable in any degree (highly, semi, . . . ) or agent specific and can serves as a depot of drug to be slowly released outwards especially in ICU patients.

3—The outermost cuff (external cuff) (C3, FIG. 3) has pores and/or holes in it to serve as immediate releasing depot of drug outwards to bring into direct contact with the mucosal layers of the tracheal lining.

According to another embodiment of the present invention, the cuff(s) of the present invention and their pilot balloons (FIG. 1, $P_1$-$P_n$ and $P'_1$-$P'_n$) can be designed to be built fixedly on the ETTs and/or devices mentioned above, or they can be built in a modular way so they can be installed on the conventional, existing devices for the above mentioned applications, or any other possible future applications.

According to a preferred embodiment of the present invention, the cuffs are preferred, to be built fixedly on the ETT(s) and or devices of desire.

According to another embodiment of the present invention, in the case of designing the modular cuffs to be mounted on the existing devices, the cuffs may also, as in the case of the fixed multiple cuffs built on the body of the apparatus, have different symmetric and asymmetric shapes with different pore and/or hole characteristics located symmetrically or asymmetrically at one side, both sides, and be of different sizes, shapes and diameters.

According to another embodiment of the present invention, each cuff of the present invention can also be made of different materials, and have different orifices in order to have the capability to be installed over different locations on linear (FIGS. 1 a-c), bent (FIG. 1, d), and/or circular tube(s) with connections to other tubes.

Figure 1:
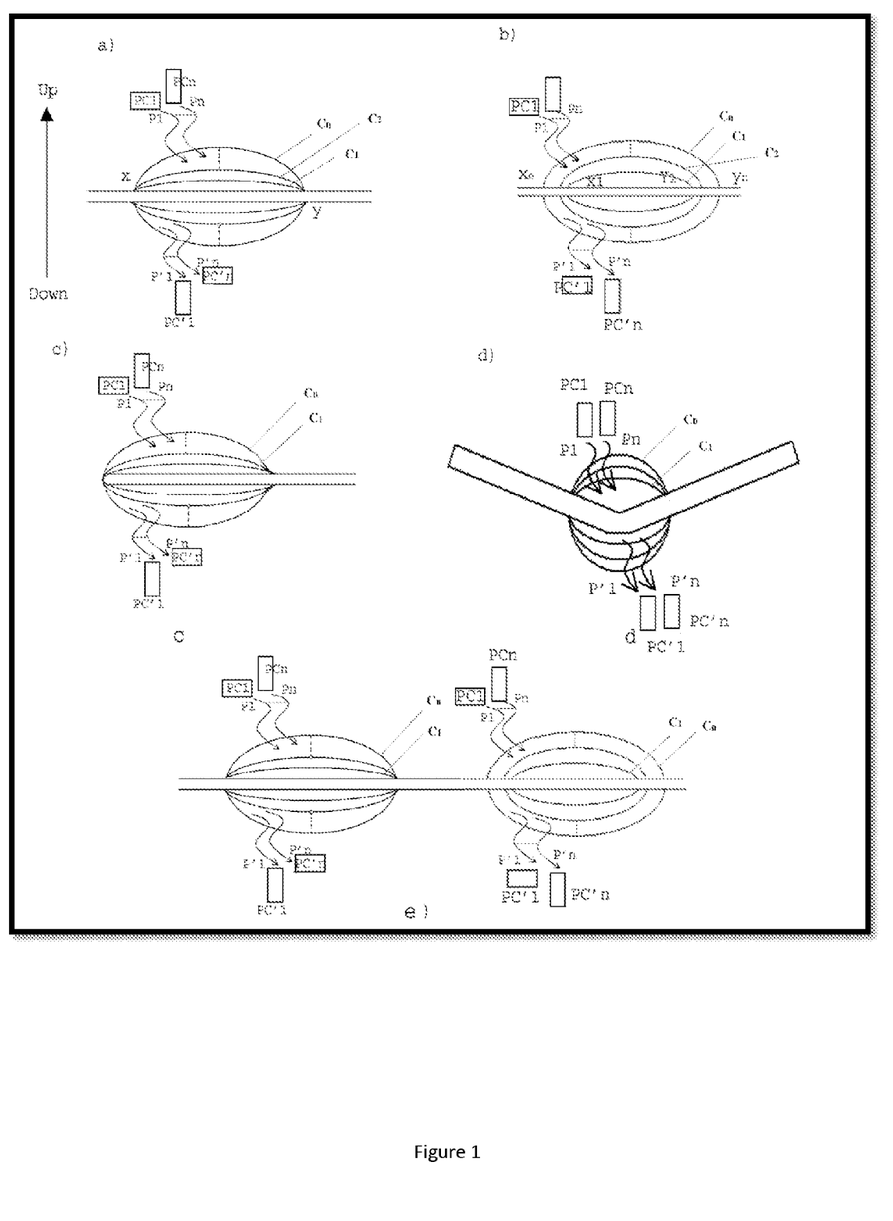
FIG. 1 is a schematic presentation of the design of the multiple cuff of the present invention.

According to another embodiment of the present invention, the installation location of the embedded cuff(s) of the present invention on ETTs, or any of the above-mentioned devices, can be either the same as the layers below (FIG. 1 a x-y ), or on different symmetric and/or asymmetric positions (FIG. 1, b, $x_1$-$y_1$-$x_n$-$y_n$).

One or several of the cuff(s), according to other preferred embodiments of the present invention, can be installed on any desired device in which case properties of each cuff can be the same or different (FIG. 1, e).

In the case of the application of multiple cuffs on a device it is preferred that the cuff properties of the two or more cuffs be different.

According to a more preferred embodiment of the present invention, in case of preferring to install the cuff before (proximal to i.e. back to back or side by side) the main cuff of the device of desire [e.g. ETT (FIG. 2)], the cuff before the original one (proximal cuff) (C1, FIG. 2) is preferred to be perforated or permeable in any degree (highly, semi, . . . ) to let the drugs of desire leave it during the application. This will help the drug flow forward (in the case of ETTs), anesthetizing the areas in contact with the main distal cuff and any predetermined area (C2, FIG. 2).

According to another embodiment of the present invention, in any case (e.g. in the case of the multiple cuff(s) built on ETTs), each cuff(s) may have its own shape and/or characteristics, and also its own number of inlets and outlets or it may be designed to jointly use the inlet(s) and/or outlet(s) of the other fixed or mounted layer(s).

According to another embodiment of the present invention, the modular cuff(s) of the present invention may be used for single use or repeated uses, depending on the material, type, application, or other effective factors.

As already mentioned above, all or some desired embodiments of the present invention can be applied on ETT(s) and/or any other apparatus in which one or several cuffs are used for the fixation, and/or drug delivery.

According to other embodiments of the present invention, in all of the above mentioned applications and any other application not mentioned above, the use of the proposed cuff system, and the consequent target delivery of anesthetics and/or other drugs of desire, will lead to a higher level of toleration of the cuffed systems, or other desired therapeutic effects caused due to the application of the desired drugs.

According to another embodiment of the present invention, the cuff systems of the present invention can have other therapeutic applications rather than delivery of drugs, such as expansion of blocked and/or narrowed arteries, or extraction of objects blocking and/or fixed within different channels.

According to another embodiment of the present invention, multiple cuffs of the present invention can also be used for the delivery of drugs such as thrombolytic materials through an appropriately designed cuff(s) located at the end of the Fugarty (Fogarty) catheters, and vasoconstrictors/sclerotherapy in Blackmore catheters, or treatment of varicose veins in limbs and so on and in sampling pulmonary secretions from intubated patients suspected of having pneumonias, cystic fibrosis or the device can be used for long term instillation of drugs e.g. for intubated ICU patients.

According to another embodiment of the present invention, the multiple cuffed systems resulting from the embodiments of the present invention can also be used in conditions like angiofibroma, esophageal varices and hemorrhoids by anesthetizing the target area initially, and later on injecting the sclerosing agents.

Similarly the application of the multiple cuff(s) also appears to be of value in coronary artery stenosis causing their dilatation and concomitant role and feasibility of drug injection such as heparin, fibrinolytic and antithrombotic agents, etc.

The embodiments of the present invention can also be used for the application of double cuffed tubes in various sizes & shapes for injecting drugs (e.g. vasoconstrictors) locally to patients with epistaxis anywhere in the nasopharyngeal area.

One of the most preferred applications of the cuff(s) of the present invention is their application on ETTs. The resulting ETT(s) (FIGS. 2-5) have multiple cuff(s), each cuff having separate inlet and outlet or pilot balloons with unidirectional valves. The different cuff may also have pores and holes of different sizes and shapes or may be permeable in any degree (highly, semi, ... ). The holes and pores of each cuff can have different sizes, and the cuffs may be used in a way that any different cuff of any pore and/or hole size may be located below or over any other cuff of interest.

The new multiple cuffed ETT can have any number of required pilot balloons with unidirectional valves that can be used for different purposes including the inflation of the cuffs and or injecting or circulating different substances in their liquid and/or gaseous states.

The multiple cuffed ETT of the present invention may have different sizes and shapes, can be made using different polymeric, organic and or composites and can be used for any other purposes in different parts of the body, in order to perform the normal functions of normal cuffed instruments, or other functions such as local delivery and spraying of single, or drug mixtures.

The multiple cuffed ETT can be designed to have one or more cuff(s), each having different sizes and dimensions. Each cuff may also be designed to have symmetrical or asymmetrical shapes and/or cuff properties (FIGS. 1 a-e), in order to meet the requirements of any special or general case.

Therefore it is an object of the present invention to design an ETT to solve the problems encountered during the application of the traditional ETTs, which were mentioned above. According to an embodiment of the present invention the new cuff system of the ETT tube, can handle the local delivery of any anesthetic, or any other medication, in the periphery of the cuffs in the traditional ETT, multiple cuffs in any especially tailored ETT, or any other desired locations in promoting drug delivery.

According to another preferred embodiment of the present invention, the multiple cuff system for local delivery of the desired drugs, comprises one or several cuff(s), each cuff of which can have one or several pilot balloons (FIG. 1, $P_1$-$P_n$ and $P'_1$-$P'_n$) that can be used for expansion of the cuff, or its outer layer, for the injection of one or several drugs of liquid, gas, suspension, or gel drugs for different purposes, or in order to wash one or all of the cuffs for any further applications.

According to another embodiment of the present invention the different cuff(s) ($C_1$-$C_n$, a FIG. 1) may be made of different biocompatible or non-biocompatible organic, inorganic, composite, or polymeric compounds where the non-biocompatible layers can be used provided that they do not contact the internal organs of the body, or any sensitive external parts, either as the lower layers of the cuff, or with some means in avoiding direct contact.

According to another embodiment of the present invention, the material selected for the cuffs can be either porous materials of different pore sizes, the pore sizes of which may be selected so that they are either equal or different in different cuff(s), or the cuffs are mechanically and/or electrochemically and/or optically and/or using any other suitable techniques perforated in the same or different, homogenous or non-homogenous way in order to let the drug(s) inside each of which enter the outer (external) cuff or finally the tissues in contact, in a reasonable distance or in the vicinity of the cuff(s).

According to another preferred embodiment of the present invention, any of the intact cuff(s) of the present invention, are of the so-called high-volume and low-pressure type in order to avoid probable damages to the ETT, to make it easier to leave the anesthesia state, and also to make it easier for the patient to tolerate the tube.

It is noteworthy that, ETT(s) always have a fixed conformation which is in a form that always a certain half circle of all ETTs [and hence a certain half circle of the cuff(s)] can be in contact with the lower part of the inner layer of the respiratory channel, (FIG. 1 a-e the lower hemisphere) and the other half circle of the tube is, as a result, in contact with upper part of the inner layer of the respiratory channel. As a result the distribution of the pores and/or holes on the cuff(s) may be required to be designed in certain patterns depending on the type and physical state of the drugs to be used.

According to what is said about the size, and/or number of the holes and/or pores on the parts of the cuff of the present invention in touch with respiratory channel are preferred to be chosen so that in case of the application of liquid drug(s), which will gather at the lower half of the cuff (FIGS. 1 a-e, the upper hemisphere) due to gravity, a moderate amount of the drug can leave the lower holes. Naturally trickle at the lower part of the inner layer of the respiratory channel.

It is also preferred that the number of holes in upper hemisphere (FIGS. 1 a-e,) of cuff be more or their sizes be larger, according to most preferred embodiments of the present invention, in order to increase the area to which the delivery of the drug is desired.

Taking this into account, according to another embodiment of the present invention, the material of the different cuff(s), or the perforating means can be chosen so that the holes or pores in the lower half circle of the tubes are smaller than those of the upper circle. This will, in case liquid drugs are filled in one or some of the layers of the cuff(s), avoid more diffusion of the drug, which is accumulated at the lower half circle of the cuff(s) due to gravitational effects, to the lower part of the inner layer of the respiratory channel. The application of the cuff system of the present invention is preferred to be according to one of the following conformations.

A: Multiple-Cuffed Devices

In this case it is preferred that more than one of the cuff(s) of the present invention be installed or built on the device of desire (FIG. 1 e, and FIGS. 2-5).

In the case of the existence of more than one cuff, each cuff can have pores/holes on it or may be permeable in any degree (highly, semi, . . . ) ($C_1$-$C_n$ FIG. 2-5).

Figure 2:
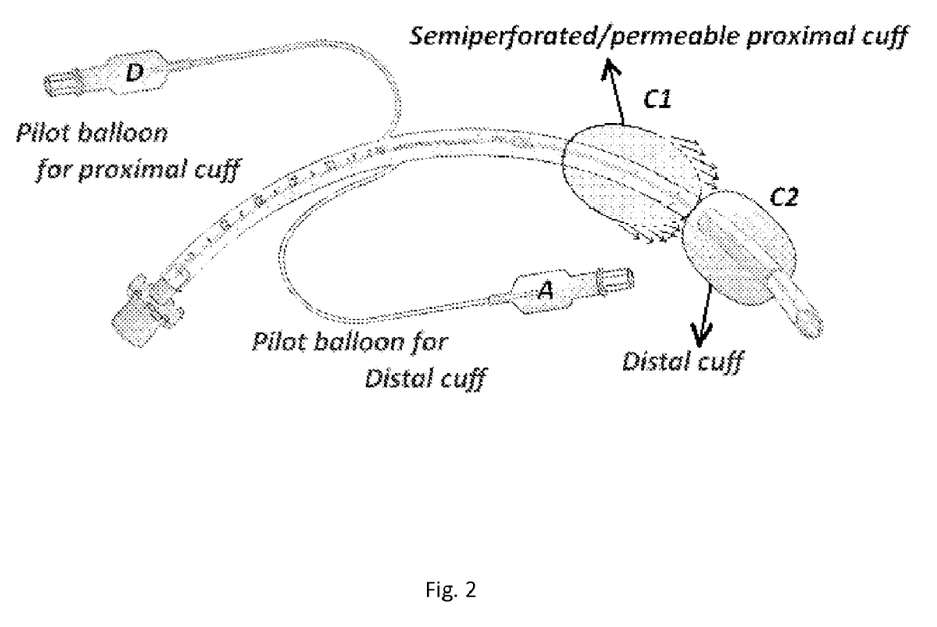
FIG. 2 illiterates a two cuffed endotracheal tube according to an embodiment of the present invention having a two side by side single cuff ($C_1$ for Drug injection, and $C_2$ for Fixation) and one pilot balloon for each cuff (A, D), or in a reverse order ($C_1$ for Fixation and $C_2$ for drug injection).
Figure 4:
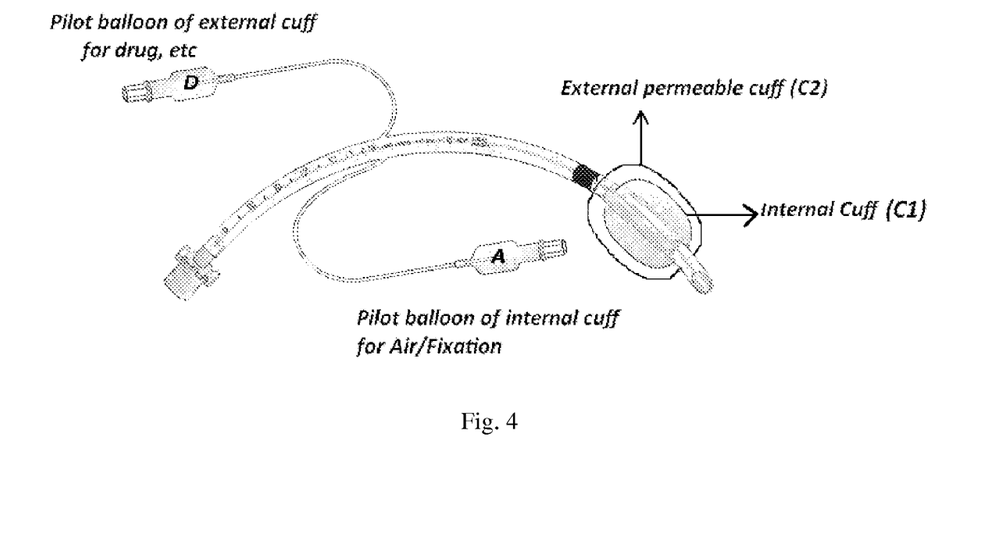
FIGS. 4&5 illustrate a two cuffed endotracheal tube according to a preferred embodiment of the present invention having a two embedded cuff ($C_1$ and $C_2$) and one pilot balloon for each cuff (A, D).
Figure 5:
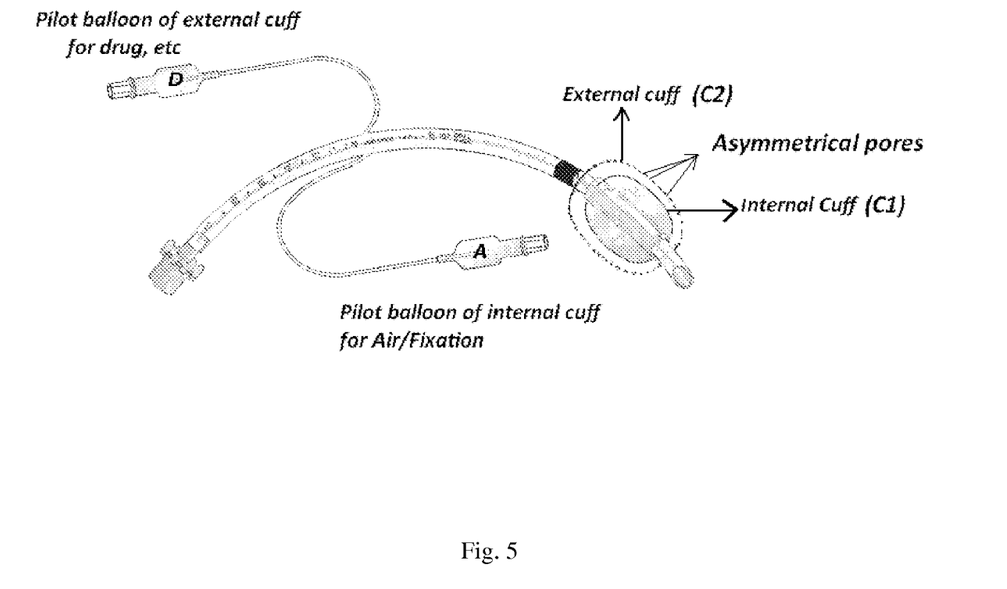

According to an embodiment of the present invention, in the case of the application of more than one cuff, the number of cuff(s) is preferred to be two (FIGS. 2, 4 & 5).

Figure 3:
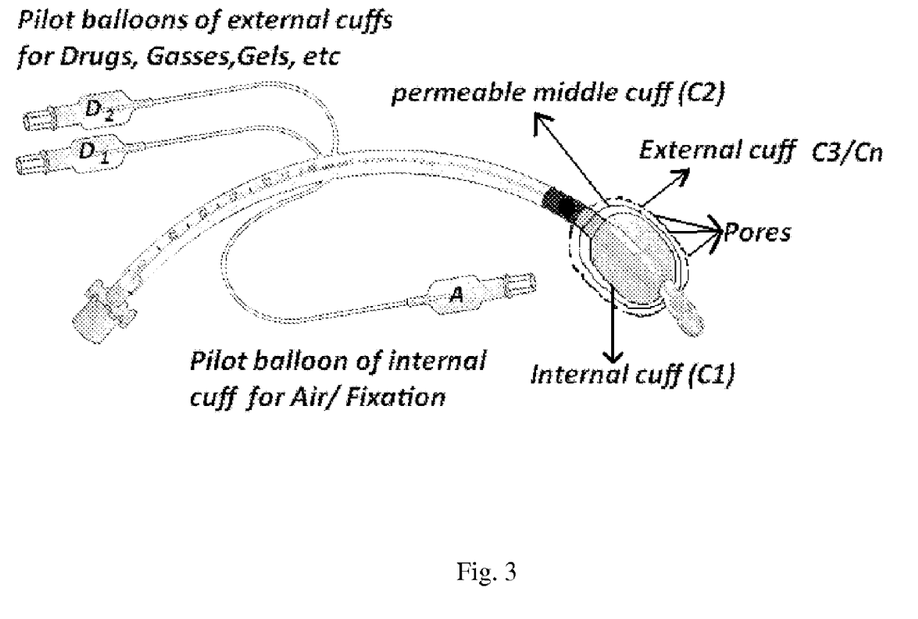
FIG. 3 illustrates an endotracheal tube according to an embodiment of the present invention having a three cuff (C1-C3) and three pilot balloons (A, D1, and D2).

According to another preferred embodiment of the present invention, in the case of the application of more than one cuff, one of them can have pores and/holes in their layer or middle one can be permeable in any degree(highly, semi, . . . ) or agent specific (FIG. 3).

According to another preferred embodiment of the present invention in the case of the application of two cuffs it is preferred that one of the cuff(s) be perforated or permeable in any degree (highly, semi, . . . ) (FIGS. 2, 4 & 5), while the other one is impermeable and is used for fixation process. In this case the perforated or permeable cuff is the means for the delivery of the anesthetic or other drugs to the neighboring tissues of itself and also the fixation cuff.

According to another preferred embodiment of the present invention, the perforated cuff is preferred to be located before (proximal to) the fixation cuff (FIG. 2). The proximal cuff is the perforated or permeable one, whiles the distal one, is the fixation cuff). This will cause, as will be described later, the drugs of desire get the target tissues of the fixation cuff better according to a preferred application process of the present invention. As mentioned above the cuff system of the present invention, can be installed proximal to the fixation cuff (FIG. 2) in which case the application method and results may be different from the single, multi and double cuffed system of the present invention (and vice versa); After the intubation and well before the patient is aware again, the distal cuff is deflated. After suctioning oropharyngeal area while the drug of desire (e.g. local anesthetic), which is injected to the proximal cuff, leave it through its holes or permeable layer. Following the instillation of the anesthetic into the proximal cuff, and spraying most of the drugs from the surface, the distal cuff is re-inflated via its own pilot balloon for re-fixation of tracheal tube and preparing for extubation.

According to a preferred method of the application of the multi cuffed system (FIG. 2-5) of the present invention, the following method can be used for the delivery of the drug to the target tissue:

One should first fill the drug delivery cuff with a proper locally administrable anesthetic drug or a mixture thereof, at any optimum temperature and/or pressure a proper time before the extubation and before the effects of the anesthetics on the patient wears off. (It is noteworthy that at this stage the fixation cuff, is inflated). The fixation cuff(s) is then deflated. A Suction step must be performed before deflation to avoid probable risks.

The drug in the delivery cuff is then forced to leave from the drug delivery cuff Air injection can be applied to facilitate the exit of the drugs. The gravitational effects cause the drug to trickle downwards, leading to the delivery of the drug to the lower parts of the respiratory passage, including the parts in touch with the fixation cuff. The next step (maybe not necessary), includes deflation and then reinflation of the inner layer (cuff) which not only helps the remaining drugs leave the outer layer of the cuff(s), but can also serve as the original cuff in conventional ETT(s). Finally the fixation cuff is re-inflated to perform its inherent role of fixation. In situations where deflation of the inner cuff is unwarranted, injection of air into the perforated cuff can help in complete emptying of the cuff containing of drug.

B: Single Cuff

In this conformation it is preferred that the cuff is either built or installed on a cuff less devices in which case its structure should be designed to perform any action done by the conventional device in addition to the new applications of the present invention, or on a conventional device.

According to the mentioned embodiment of the present invention physical and/or chemical characteristics and properties of the cuff should be chosen to meet the specified goals.

Figure 6:
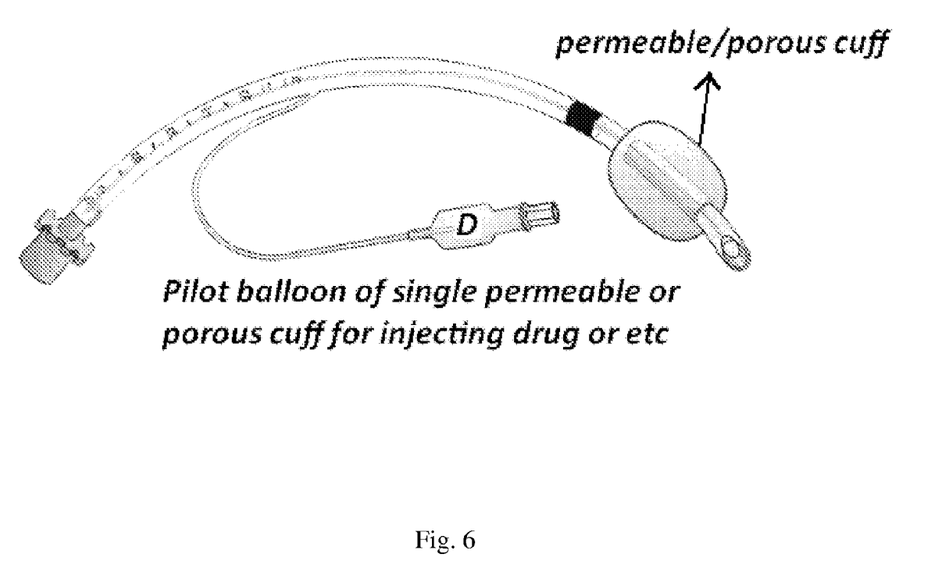
FIG. 6: Multi perforated or permeable in any degree (highly, semi, . . . ) single cuffed ETT according to a preferred embodiment of the present invention that can be used most commonly in pediatrics and little children.

A perforated/permeable in any degree (highly, semi, . . . ) cuff can be used in cuffless devices (such as pediatric cuffless ETTs) for increasing tolerance and or injection of drugs or sampling. (FIG. 6)

The fixation cuff(s) ($C_2$ FIG. 2 $C_1$ FIGS. 3-5), (no matter the second cuff is built or installed on the ETT or the other devices), is used to perform the conventional role of the cuff(s) in the ETT, and also to help the residues of the drug in the outer cuff(s) be better sprayed to the target tissue.

The multiple cuffed ETT of the present invention can be used for elective and urgent/emergent surgeries due to its innumerable advantages elaborated above.

According to another preferred method of the application of the single cuffed ETT of the present invention the disadvantages of the conventional tubes are avoided, and the best performance of the new cuff systems are achieved by:

First filling the cuff with a proper locally administrable anesthetic drug or a mixture thereof (FIG. 6) through its pilot balloon, a proper time before the extubation and before the effects of the anesthetics on the patient wears off, and then, letting a locally administrable drug leave it through the holes and/or pores or permeable layer present on it.

The drugs that can fulfill the goals of the present invention include a mixture of drugs or other gaseous or liquid materials.

In case the pores in the cuff(s) are small, or in case the diffusion of the drug through the pores and/or holes or permeable layer is relatively slow, the drugs can be injected to the cuff after prior preheating, to a required temperature.

According to another embodiment of the present invention the overall system can be automatized.

According to another embodiment of the present invention, regarding the fact that ETT(s) or other devices, on which the cuff system of the present invention is applied, the patients do not suffer the disadvantages of the conventional ones, more cuffs can be built on the tubes and devices using the present invention, to achieve any further desired goals.

Each cuff of present invention has its own pilot balloons ($P_1$-$P_n$ and $P'_1$-$P'_n$ FIGS. 1, a-e), connected to pressure release valves ($PC_1$-$PC_n$ and $PC'_1$-$PC'_n$ FIG. 1, a-e) (The presence of the mentioned pressure release valve(s) for the inlet(s) and/or outlet(s) of the cuff(s) helps avoid the development of excessive pressure in the layer(s) of the cuff which may be dangerous.

The existence of these pressure release valves provides the option of controlling the pressure of each cuff, which depending on the application may have certain tolerability limits. Each outlet and/or inlet can be controlled using different apparatus ranging from hypodermal syringes, to dosing pumps, warmers or infusers.

The goals of the present invention are further reached by preferably designing two cuffs on the body of any ETT, laser SLT (Single Lumen Tube), double lumen(s), Bronchial Blocker(s), RAE, Tracheostomy tubes, Supra glottic instruments, or any other apparatus in which cuff(s) are used either for fixation purposes and used for or needed for the delivery of drugs. The innermost cuff ($C_1$ FIGS. 1 a-e) is preferred to be gas and/or liquid impermeable, while the outermost cuff ($C_n$ FIGS. 1 a-e) may have pores and/or holes or permeable surface (in any degree) on it to let the drug leave them and reach the tissues in touch or in proximity with the cuff.

According to another embodiment of the present invention the path from the pilot balloon to the cuff and even as farther as the tip of the tube and may either be porous and/or perforated or permeable in any degree(highly, semi, . . . ) so that the injected drugs are also delivered to the tissues in farther vicinity from the fixation cuff. The ETT's lumen (whole tube or a part thereof) can be designed to have two layers (or multilayer) to facilitate the exit of desired drugs through the pores or permeable outer layer in order to anesthetize all over the tracheal tract, and even between cuff and the bevel. It is noteworthy that the traditional ETTs cannot be used for the delivery of drugs of any kind to the in-touch tissues.

The cuffs may have different shapes, sizes and/or positions. The shape of the cuffs may range from cylindrical, to round to elliptical, while they are preferred to have the typical elliptical structure as in typical ETTs, while depending on the application of the multiple cuff(s) in other apparatus they may change in shape to meet the required needs.

The position of the cuff(s) may vary from the beginning (FIGS. 1, a and b) to the end of the apparatus, (FIG. 1, c), or at bent parts of the tubes (FIG. 1, d), depending on the needs.

In the case of the typical ETTs, the cuffs are preferred to be positioned in the normal location of cuff as in typical ETTs, while depending on the application of the multiple cuff(s) in other apparatus they may change in position to meet the required goals.

As mentioned before, each cuff may be impermeable, porous or perforated, or permeable in any degree (highly, semi, . . . ) or a combination thereof, depending on the material to be used in their construction, and each cuff may be made of the same or different materials than the other cuffs. In case the cuffs are porous or are mechanically, electronically, optically (or according to any other proper methods) perforated, the size and dissemination of the pores and/or holes on them can be all the same or can vary within each cuff and/or from one cuff to the other.

In case the sizes of the pores and/or holes in the different cuffs are different, any sequence of cuffs may be used in the design, depending on the probable application of the apparatus.

Different composite, polymeric, organic and/or inorganic material or a mixture thereof can be used in the construction of the cuff(s), and/or the whole apparatus.

The different cuff(s) may also be chosen from materials, or the pore sizes may be chosen in a range that the cuff(s) are selectively permeable to only one, or a certain group of drugs.

As regards the present invention all biocompatible and/or mechanically flexible and/or durable polymeric materials can be used in order to make the cuff(s).

It should also be noted that in case more tissues are to be subjected to drug delivery, the intratracheal path from the pilot balloon to the cuff(s) can also be perforated in order to increase the delivery area.

It is preferred to use poly vinyl chloride membranes as the cuff(s), and in case the cuff(s) and/or desired to be drug permeable they should better be perforated using different mechanical, electrical, and/or optical methods.

The size of the holes can be in the range of 0.001 micrometer to 5 mm, preferably insulin needle bevel size and the number of pores all over the cuff can be in range of two to an infinite number in the case of the present invention.

Different drugs and/or mixture thereof can be delivered to the target tissues that are touching the cuff(s) and/or in their vicinity, via being injected to a layer of the cuff, and leaving the layer through its pores and or holes.

In the case of the present invention the drugs are preferred to be one or a combination of drugs such as local anesthetics (LA) alkalinized LA and aerosolized drugs and or other tracheal mucosa compatible drugs or gasses, as anesthetics so that the areas around the cuff are anesthetized and the pain is eliminated.

According to the most preferred embodiment of the present invention, local anesthetics such as lidocaine are injected to the second cuff to reduce the mentioned pain and intolerance.

The mentioned drugs can be used with or without pretreatments like heating to a desired and suitable temperature, or being mixed with one or a combination of reagents in order to increase the efficiency of their diffusion to the tissues in touch with the cuff.

The embodiments of the present invention, and the efficiency of the drug delivery is so valuable that the drugs can be used, in contradistinction to the previous efforts, in dosages far lower than the toxic dosage of the drugs, especially the local anesthetics, which eliminates the risks due to the high dosages or the probable burst of the cuffs in the conventional apparatus and methods.

The diffusion/permeation of the drug through the holes and/or pores of the layers can also be further facilitated by means of using aseotropic mixtures of drugs with other harmless reagents, external pressure, or by means of inflating the below and/or above cuffs.

During the application of the apparatus, which according to a preferred embodiment of the present invention is a double cuffed ETT, the outer cuff of which is perforated or permeable in any degree(highly, semi, . . . ) to let the drug leave the surface, any desired sequences can be used for the utilization of the system. Our newly designed multiple cuffs, as mentioned above, are installable on any ETT or other medical devices.

The foregoing description is illustrative of the invention described herein and should not be used to unduly limit the scope of the invention or the claims. Since many embodiments and variations can be made while remaining within the spirit and scope of the invention, the invention resides wholly in the following claims.

I claim:

1. A medical apparatus for distributing a predetermined amount of foreign substance to a predetermined area in living body comprising:

A main tube;

A first cuff wherein said first cuff comprises of a predetermined size, a predetermined shape and a material wherein said material is intact or impermeable;

A second cuff wherein said second cuff comprises of a predetermined size, a predetermined shape, porous material and/or permeable material or combination thereof, wherein said first cuff is embedded in said second cuff and wherein said second cuff serves as a depot of drug to be released to patients and wherein said second cuff allows equal distribution of a predetermined amount of a drug to a predetermined area in a living body;

A third cuff wherein said third cuff comprises of a predetermined size, a predetermined shape and made of material wherein said material consists of porous materials and wherein said first cuff and said second cuff are entirely embedded in said third cuff and wherein said third cuff serves as an immediate releasing depot of a drug outwards to bring said drug into a direct contact with a predetermined area and wherein said second cuff allows equal distribution of a predetermined amount of drug to a predetermined area in a living body;

A first tube comprising a pilot balloon wherein said first tube is implanted to said main tube for allowing a delivery of a predetermined amount of air into said first cuff;

A second tube comprising a pilot balloon wherein said second tube is implanted to said main tube for allowing a delivery of a predetermined amount of foreign substance to said second cuff;

A third tube comprising a pilot balloon wherein said third tube is implanted to said main tube for allowing a delivery of a predetermined amount of foreign substance to said third cuff.

2. An apparatus as claimed in claim 1, wherein said second cuff allows equal distribution of said predetermined amount of foreign substance to said predetermined area in living body.

3. An apparatus as claimed in claim 1, wherein said second cuff is in proximal position with respect to said first cuff.

4. An apparatus as claimed in claim 1, wherein said second cuff is in distal position with respect to said first cuff.

5. An apparatus as claimed in claim 1, wherein said third cuff allows equal distribution of said predetermined amount of foreign substance to said predetermined area in living body.

6. An apparatus as claimed in claim 1, wherein said pilot balloon of said second and said third tube distributes said predetermined amount of foreign substance to said predetermined area in living body in a unidirectional manner.

7. An apparatus as claimed in claim 1, wherein said second cuff and said third cuff have mutually different physical and/or chemical properties, different shapes, different installation properties, different number of inlets and outlets based on an application.

8. An apparatus as claimed in claim 1, wherein said second cuff and said third cuff are modular cuffs.

9. An apparatus as claimed in claim 1, wherein said second cuff and said third cuff have a number of pilot balloons with unidirectional valves to inflate cuffs, inject or circulate foreign substance in liquid and gaseous states.

10. An apparatus as claimed in claim 1, wherein said second cuff and said third cuff have pressure relief valves for the inlets and the outlets to avoid development of excessive pressure in said second cuff and said third cuff.

* * * * *